United States Patent [19]

Franck-Neumann et al.

[11] 4,233,129

[45] Nov. 11, 1980

[54] PROCESS OF PREPARATION OF ALKYL ESTERS OF DL CIS CHRYSANTHEMIC ACID

[75] Inventors: Michel Franck-Neumann; Christiane Dietrich-Buchecker, both of Strasbourg; Michel Miesch, Mulhouse, all of France

[73] Assignee: Roussel Uclaf, Paris, France

[21] Appl. No.: 59,291

[22] Filed: Jul. 20, 1979

[30] Foreign Application Priority Data

Jul. 24, 1978 [FR] France ................................ 78 21814

[51] Int. Cl.³ ............................................ B01J 19/08
[52] U.S. Cl. ................................ 204/158 R; 560/124
[58] Field of Search ...................... 204/158 R; 560/124

[56] References Cited

U.S. PATENT DOCUMENTS

| | | | |
|---|---|---|---|
| 3,657,086 | 4/1972 | Matsui et al. | 204/158 R |
| 3,674,832 | 7/1972 | Sherlock et al. | 204/158 R |
| 4,085,273 | 4/1978 | Peterson et al. | 560/124 |

*Primary Examiner*—Howard S. Williams

*Attorney, Agent, or Firm*—Hammond & Littell, Weissenberger and Muserlian

[57] ABSTRACT

A process for the production of an alkyl ester of dl cis chrysanthemic acid having the formula

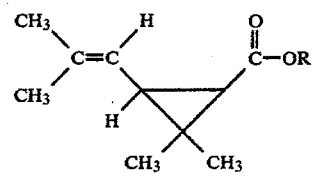

wherein R is an alkyl having from 1 to 6 carbon atoms, involving preparing a lithiated derivative of 2-methylpent-2-en-4-yne, reacting the same with an alkyl chloroformate, optionally reducing the acetylenic bond to an ethylenic bond, reacting the alkyl ester with diazo-2-propane, irradiating or heating the resultant pyrazole carboxylate and, if not previously reduced, subjecting the resultant cyclopropane carboxylate to the action of a reducing agent.

10 Claims, No Drawings

PROCESS OF PREPARATION OF ALKYL ESTERS OF DL CIS CHRYSANTHEMIC ACID

The present invention relates to a process for the production of alkyl ester of dl cis chrysanthemic acid.

OBJECTS OF THE INVENTION

An object of the present invention is to develop a process for the preparation of alkyl esters of 2,2-dimethyl-3RS-(2'-methyl-1'-propenyl)-cyclopropane-1SR-carboxylic acid, or alkyl esters of dl cis chrysanthemic acid having the formula

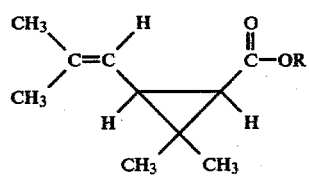

wherein R is an alkyl having from 1 to 6 carbon atoms consisting of essentially of the steps of (A) reacting methyl lithium with 2-methyl-pent-2-en-4-yne in an inert organic solvent, (B) reacting the lithiated derivative obtained with a $C_{1-6}$ alkyl chloroformate at a temperature below 0° C. in an inert organic solvent, (C) recovering an alkyl ester of an unsaturated acid having the formula

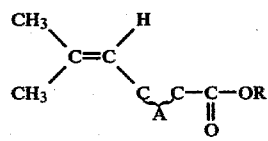

wherein R has the above assigned values and $\widetilde{A}$ represents a carbon to carbon bond selected from the group consisting of an ethylenic bond and an acetylenic bond, (D) reacting said alkyl ester of an unsaturated acid with diazo-2-propane at a temperature below 0° C. in an inert organic solvent, to obtain when $\widetilde{A}$ is an acetylenic bond a mixture of compounds having the formula selected from the group consisting of

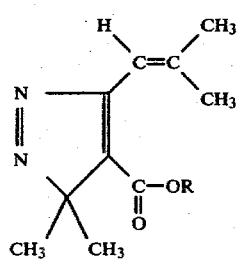

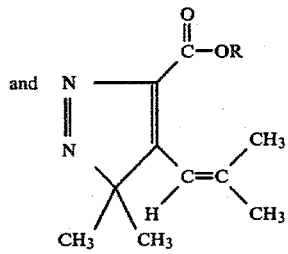

which can be separated and when $\widetilde{A}$ is an ethylenic bond, a mixture of compounds having the formula selected from the group consisting of

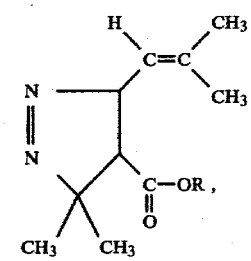

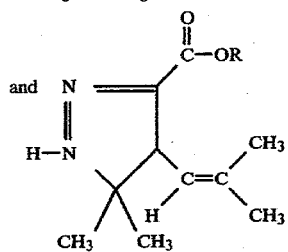

which are separated, (E) subjecting the alkyl ester of formula 1,2, mixtures thereof or 3 to a process selected from the group consisting of irradiation and heating for the compound of formula 3 or to an irradiation for the compounds of formula 1,2 or mixtures, and (F) recovering said alkyl esters of dl cis chrysanthemic acid.

This and other objects of the invention will become more apparent as the description thereof proceeds.

DESCRIPTION OF THE INVENTION

The present invention relates notably to a process for the preparation of alkyl ester of 2,2-dimethyl-3RS-(2'-methyl-1'-propenyl)-cyclopropane-1SR-carboxylic acid, or the alkyl esters of dl cis chrysanthemic acid, of the formula I

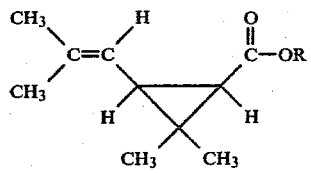

in which R represents alkyl having from 1 to 6 carbon atoms, characterized in that a 3,3-dimethyl-2-(2'-methyl-1'-propenyl)-1-(alkoxycarbonyl)-cyclopropane of the formula VI

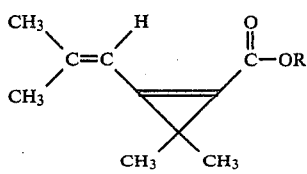

VI in which R has the above-noted values, is reacted with a reducing agent selected from the group consisting of hydrogen in the presence of nickel boride, hydrogen in the presence of palladium deposited on calcium carbonate and diimide.

In addition the desired alkyl ester of dl cis chrysanthemic acid can be prepared by a total synthesis where a stereospecific cyclopropane is formed by irradiation or heating of a pyrazole carboxylic acid.

More particularly therefore, the present invention relates to a process for the preparation of alkyl esters of 2,2-dimethyl-3RS-(2'-methyl-1'-propenyl)-cyclopropane-1SR-carboxylic acid, or alkyl esters of dl cis chrysanthemic acid having the formula

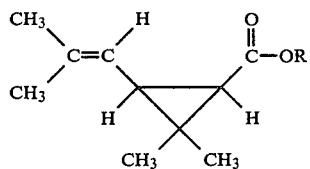

wherein R is an alkyl having from 1 to 6 carbon atoms consisting essentially of the steps of (A) reacting methyl lithium with 2-methyl-pent-2-en-4-yne in an inert organic solvent, (B) reacting the lithiated derivative obtained with a $C_1$–$C_6$ alkyl chloroformate at a temperature below 0° C. in an inert organic solvent, (C) recovering an alkyl ester of an unsaturated acid having the formula

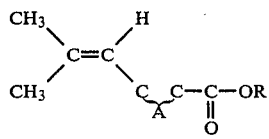

wherein R has the above assigned values and $\widetilde{A}$ represents a carbon to carbon bond selected from the group consisting of an ethylenic bond and an acetylenic bond, (D) reacting said alkyl ester of an unsaturated acid with diazo-2-propane at a temperature below 0° C. in an inert organic solvent, to obtain when $\widetilde{A}$ is an acetylenic bond a mixture of compounds having the formula selected from the group consisting of

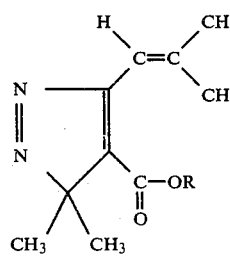

(1)

-continued

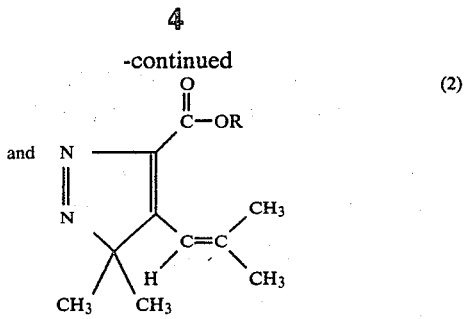

(2)

which can be separated and when $\widetilde{A}$ is an ethylenic bond, a mixture of compounds having the formula selected from the group consisting of

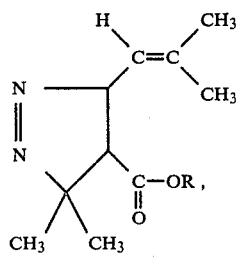

(3)

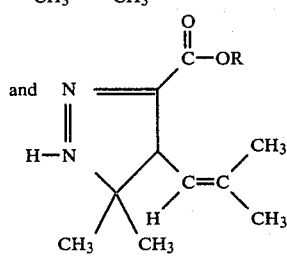

(4)

which are separated, (E) subjecting the alkyl ester of formula 1,2, mixture thereof or 3 to a process selected from the group consisting of irradiation and heating for the compound of formula 3 or to an irradiation for the compounds of formula 1,2 or mixtures, and (F) recovering said alkyl esters of dl cis chrysanthemic acid.

When reducing the compound of formula VI to give the desired compound of formula I, if the reduction is effected by halogen in the presence of a catalyst, preferably nickel boride "P-1" prepared in situ according to the method of Brown, J. Org. Chem. 35, 1900, (1970) is employed. When the reduction is effected by diimide, preferably diimide is prepared in situ according to the method of Van Tamelen et al, J.A.C.S. 83, 3725 (1961).

The product to be reduced, 3,3-dimethyl-2-(2'-methyl-1'-propenyl)-1-(alkoxycarbonyl)-cyclopropene (VI) is obtained by (A) reacting methyl lithium with 2-methyl-pent-2-en-4-yne (II).

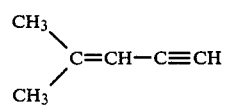

II (B) then subjecting the resultant lithiated derivative to the action of an alkyl chloroformate to obtain an alkyl ester of 5-methyl-hex-4-en-2-ynoic acid (III) of the formula

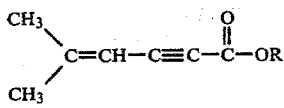

in which R represents alkyl having from 1 to 6 carbon atoms, (C) reacting this compound (III) with diazo-2-propane in order to obtain a mixture of the alkyl ester of 3,3-dimethyl-5-(2'-methyl-1'-propenyl)-3H-pyrazole-4-carboxylic acid (IV) of the formula

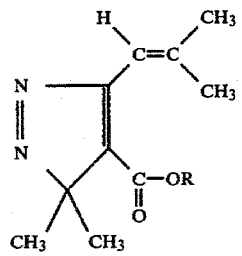

and the alkyl ester of 3,3-dimethyl-4-(2'-methyl-1'-propenyl)-3H-pyrazole-5-carboxylic acid (V) of the formula

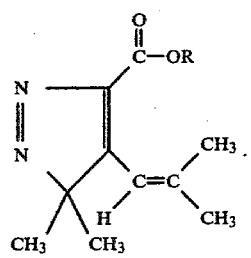

which can be separated, if desired, (D) then submitting the compound of formula IV, or the compound of formula V, or their mixture to irradition, (E) then isolating the desired compound of formula VI.

At the end of the above process, the desired product of the formula VI is obtained in admixture with varying amounts of a product of the formula VII.

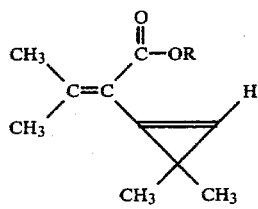

From this mixture of products of formulas VI and VII, the product of formula VI can be isolated, if desired, by customary methods such as chromatography.

The methyl ester of 5-methyl-hex-4-en-2-ynoic acid (III, R=CH₃) is preferred as the alkyl ester, and is obtained by introducing an ethereal solution of the lithiated derivative of 2-methyl-pent-2-en-4-yne into an ethereal solution of methyl chloroformate at a temperature of −55° C.±20° C. The other alkyl esters can be prepared in an analogous manner utilizing the desired alkyl chloroformate.

The mixture of the preferred methyl ester of 3,3-dimethyl-5-(2'-methyl-1'-propenyl)-3H-pyrazole-4-carboxylic acid (IV, R=CH₃) and methyl ester of 3,3-dimethyl-4-(2'-methyl-1'-propenyl)-3H-pyrazole-5-carboxylic acid (V, R=CH₃) is obtained by introducing an ethereal solution of diazo-2-propane into an ethereal solution of the methyl ester of 5-methyl-hex-4-en-2-ynoic acid (III, R=CH₃), at a temperature of −60° C.±20° C. Starting from other alkyl esters of 5-methyl-hex-4-en-2-ynoic acid, in an analogous manner mixtures of these alkyl esters of 3,3-dimethyl-5-(2'-methyl-1'-propenyl)-3H-pyrazole-4-carboxylic acid and 3,3-dimethyl-4-(2'-methyl-1'-propenyl)-3H-pyrazole-5-carboxylic acid can be obtained.

The preferred 3,3-dimethyl-2-(2'-methyl-1'-propenyl)-1-(methoxycarbonyl)-cyclopropene (VI, R=CH₃) (or its mixture with methyl 2-(3,3-dimethyl-cyclopropan-1-en-2-yl)-3-methyl-2-butanoate) is obtained by irradiation, preferably by utilizing a mercury vapor lamp, Philips HPK 125, while operating at +15° C.±10° C. in an inert organic solvent.

The starting compound of the previous synthesis, 2-methyl-pent-2-en-4-yne (II) can be prepared according to the method of Mondon, Ann. 577, 181–201 (1952) by heating 2-methyl-2-hydroxy-pent-4-yne in the presence of potassium acid sulfate.

The invention also relates to a variant in the above process but encompassed in the overall description of the process, for the production of esters of formula I, characterized in that (A) a compound of formula III

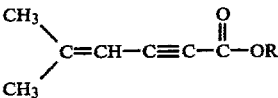

where R is an alkyl having from 1 to 6 carbon atoms is subjected to the action of a reducing agent whereby an alkyl ester of 5-methyl-hexa-2,4-dienoic acid of the formula VIII

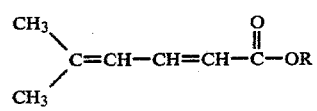

where R has the above significance, is obtained, (B) reacting the compound of formula VIII with diazo-2-propane in order to obtain a mixture of an alkyl ester of 4,5-dihydro-3,3-dimethyl-5-(2'-methyl-1'-propenyl)-3H-pyrazole-4-carboxylic acid (IX) of the formula

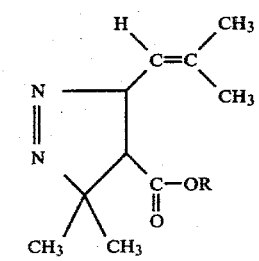

and the alkyl ester of 4,5-dihydro-5,5-dimethyl-4-(2'-methyl-1'-propenyl)-1H-pyrazole-3-carboxylic acid (X) of the formula

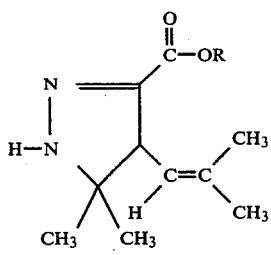

where R has the above-noted values, which mixture is separated, (C) then subjecting the compound of the formula IX to an irradiation or to the action of the heat, in order to obtain the alkyl ester of dl cis chrysanthemic acid (1) of the formula

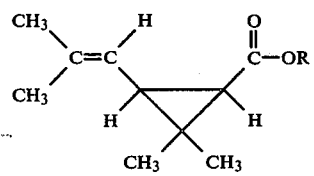

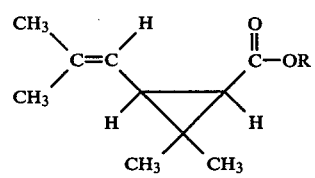

wherein R has the above-noted values.

The reducing agent which is reacted with the compound of formula III is preferably hydrogen in the presence of the Lindlar catalyst (5% palladium deposited on $CaCO_3$ containing lead acetate), but it can also be one of the other reducing agent already discussed for the reduction of the cyclopropane compound VI.

The reaction with diazo-2-propane is effected under the preferred conditions previously given.

The separation of the compounds of formulae IX and X can be effected by the usual means such as by chromatography.

The irradiation of the compound of formula IX is preferably effected under the conditions already described for the irradiation of the compounds of formulas IV and V. The denitrogenation of the compound of formula IX by heating is preferably effected at about 110° C., particularly in the presence of an inert organic solvent boiling at the desired reaction temperature, such as toluene.

For a number of years, specialists in the field of insecticides have been interested principally in trans chrysanthemic acid since only the acids of the trans configuration had the reputation of leading to insecticidal esters of sufficient activity.

Numerous total synthesis of chrysanthemic acids have been reported. These synthesis have led either to mixtures of acids of the dl cis and dl trans structure which have been low in the amount of cis acids or to acids of the trans structure.

The cis chrysanthemic acids have seen their importance increase over the past several years. They have been utilized particularly for the preparation of cyclopropane carboxylic acids having a dihalovinyl chain, whose esters possess an insecticidal activity quite superior to that of the esters of trans chrysanthemic acid (see for example French Pat. Nos. 2,185,612 and 2,240,914). The synthesis of the cis chrysanthemic acids therefore presents a very particular interest at the present time.

The process of the present invention supplying for the first time, a stereospecific total synthesis of alkyl esters of racemic cis chrysanthemic acid. This synthesis comprises only a restricted number of steps and the overall yields are high, in the order of 60% or more.

The process of the invention comprises original steps of a chemical nature. First, the specific reduction under appropriate conditions of the endocyclic double bond of the cyclopropene derivative of formula VI, without attack of the double bond of the lateral chain, leads, in a stereospecific manner with an almost quantitative yield, to the deisred alkyl ester of dl cis chrystanthemic acid, constitutes a type of reaction which has not yet been described to the present. Without the unexpected advantage of this specific reduction, all of the success of the synthesis would not have occurred.

Similarly, the reduction of the alkyl ester of 5-methyl-hex-4-en-2-ynoic acid III into the corresponding alkyl ester of 5-methyl-hexa-2,4-dienoic acid VIII under the conditions described in the invention is equally very selective and thus permits access to the pyrazolic structure under excellent conditions.

On the other hand, the fact that the irradiation of the two substituted pyrazolic derivatives IV and V leads practically solely to the single-cyclopropenic derivative also presents an original and unexpected characteristic of the invention. Dietrich-Buchecker et al, Tetrahedron, 33, 753–755 (1977) have, it is true, described an analogous phenomena but concerning pyrazolic derivatives whose substituents were different from those of the compounds of formulae IV and V of the present application. However there is no reason to expect that the phenomena noted by these authors would also occur in the case where the substituents of the pyrazole ring, as in the present case, are the groups (alkoxycarbonyl) and (2'-methyl-1'-propenyl).

The following examples are illustrative of the practice of the invention without being limitative thereof in any manner.

EXAMPLE 1

Methyl ester of 2,2-dimethyl-3RS-(2'-methyl-1'-propenyl)-cyclopropan-1SR-carboxylic acid or Methyl ester of dl cis chrysanthemic acid STEP A: Methyl ester of 5-methyl-hex-4-en-2-ynoic acid The lithiated derivative of 2-methyl-pent-2-en-4-yne was first prepared by introducing progressively, at a temperature of −15° C., 40 cc of a 5% ethereal solution of methyl lithium, into a flask cooled to −15° C. under a nitrogen atmosphere, then adding 5 gm of 4-methyl-pent-3-en-1-yne thereto progressively at a temperature below 0° C.

Next, the lithiated solution obtained above was slowly introduced into a solution of 7.5 cc of methyl chloroformate in 50 cc of ether, while maintaining the temperature below −50° C. The temperature was allowed to warm to 20° C. The reaction mixture was then poured on ice and the organic phase was separated by decanting. The aqueous phase was extracted with ether. The ethereal phases were combined, dried and concentrated to dryness. 7.86 gm of the raw methyl ester were obtained. After distillation under a vacuum of 0.1 mm of mercury, 7.44 gm of the methyl ester of 5-methyl-hex-4-en-2-ynoic acid were recovered.

STEP B: Mixture of the methyl ester of 3,3-dimethyl-5-(2′-methyl-1′-propenyl)-3H-pyrazole-4-carboxylic acid and the methyl ester of 3,3-dimethyl-4-(2′-methyl-1′-propenyl)-3H-pyrazole-5-carboxylic acid and Isolation of the constituents of the mixture 1 gm of the methyl ester of 5-methyl-hex-4-en-2-ynoic acid, obtained in Step A, was dissolved in 20 cc of ether. The solution was cooled to −60° C. 4 cc of a solution of diazo-2-propane in ethylbenzene containing 2.14 m. mols/ml, obtained according to a method analogous to that described by Dietrich-Buchecker et al, Tetrahedron, 33, p. 745–749 (1977), was added progressively thereto. The temperature was then allowed to rise to 0° C., and after the disappearance of the red color characteristic of diazo-2-propane, allowed further to rise toward +30° C. Another 1 cc of the diazo-2-propane solution was added and the reaction mixture was allowed to stand for 4 hours at about +20° C. After concentration to dryness and distillation under reduced pressure, 1.70 gm of the mixture of the methyl ester of 3,3-dimethyl-5-(2′-methyl-1′-propenyl)-3H-pyrazole-4-carboxylic acid and the methyl ester of 3,3-dimethyl-4-(2′-methyl-1′-propenyl)-3H-pyrazole-5-carboxylic acid was recovered in a proportion of 2:1 according to the MNR spectra.

After chromatography on silica gel with elution with a 9:1 mixture of petroleum ether (b.p. 40°–60° C.) and ethyl ether, 0.84 gm of the methyl ester of 3,3-dimethyl-5-(2′-methyl-1′-propenyl)-3H-pyrazole-4-carboxylic acid was obtained. Then, after further elution with a 6:4 mixture of petroleum ether (b.p. 40°–60° C.) and ethyl ether, 0.39 gm of the methyl ester of 3,3-dimethyl-4-(2′-(2′-methyl-1′-propenyl)-3H-pyrazole-5-carboxylic acid was recovered.

STEP C: 3,3-dimethyl-2-(2′-methyl-1′-propenyl)-1-(methoxycarbonyl)-cyclopropene.

(a) Irradiation of the methyl ester of 3,3-dimethyl-4-(2′-methyl-1′-propenyl)-3H-pyrazole-5-carboxylic acid The irradiation was effected at a temperature of +15° C. with a mercury vapor lamp, Phillips HPK 125, under a nitrogen atmosphere.

0.380 gm of the methyl ester of 3,3-dimethyl-4-(2′-methyl-1′-propenyl)-3H-pyrazole-5-carboxylic acid in solution in 100 cc of anhydrous ethyl ether was irradiated. When the stoichiometric quantity of nitrogen passed off (≃45 cc) which took about one hour, the irradiation was discontinued. The solvent was evaporated and 0.350 gm of raw product (which according to its MNR spectra contained solely the desired cyclopropane) was obtained. This raw product was subjected to chromatography on silica gel with elution with petroleum ether (b.p. 40°–60° C.). 0.315 gm of 3,3-dimethyl-2-(2′-methyl-1′-propenyl)-1-(methoxycarbonyl)-cyclopropane was recovered after distillation of the solvent.

(b) Irradiation of the methyl ester of 3,3-dimethyl-5-(2′-methyl-1′-propenyl-3H-pyrazole-4-carboxylic acid Irradiation of this compound under the same conditions as those utilized in paragraph (a) hereabove, led, with the same yield to 3,3-dimethyl-2-(2′-methyl-1′-propenyl)-1-(methoxycarbonyl)-cyclopropene of the same quality as that obtained in the preceeding paragraph (a).

The 3,3-dimethyl-2-(2′-methyl-1′-propenyl)-1-(methoxycarbonyl)-cyclopropane obtained according to paragraphs (a) and (b) above presents the following characteristics: MNR Spectra: in p.p.m. with reference to trimethyl silane in CDCl$_3$.

$CH_3$: 1.26 (H,6 singulet), 1.95 (H,6-doublet-constant of the linkage: J=1.5 Hz).

$CH_3CO_2$:3.75 (H,3 singulet), Vinylic H: 6.28 (H, 1 heptaplet, J≃1.5 Hz).

(c) Irradiation of the mixture of the methyl ester of 3,3-dimethyl-5-(2′-methyl-1′-propenyl)-3H-pyrazole-4-carboxylic acid and the methyl ester of 3,3-dimethyl-4-(2′-methyl-1′-propenyl)-3H-pyrazole-5-carboxylic acid leads, under the conditions analogous to those utilized in paragraphs (a) and (b) above, to the production of 3,3-dimethyl-2-(2′-methyl-1′-propenyl)-1-(methoxycarbonyl)-cyclopropene with a yield in the order of 90%.

STEP D: Methyl 2,2-dimethyl-3RS-(2′-methyl-1′-propenyl)-cyclopropane-1SR-carboxylate or methyl dl cis chrysanthemate.

(a) Reduction by hydrogen in the presence of nickel boride "P-1"

The catalyst of nickel boride was prepared, in situ, in a hydrogenation bomb according to the method of Brown (J. Org. Chem. 35, 1900, [(1970]). 1.24 gm of nickel acetate tetrahydrate in solution in ethanol was utilized. The hydrogenation bomb was purged several times, alternatively under vacuum and under a hydrogen pressure the contents were agitated under a hydrogen atmosphere. After stopping the agitation, 1.0 gm of 3,3-dimethyl-2-(2′-methyl-1′-propenyl)-1-(methoxycarbonyl)-cyclopropene were introduced. Agitation was commenced again under a hydrogen atmosphere and 125 cc of hydrogen were absorbed in about three hours. The reaction mixture was filtered through activated magnesium silicate (florisil) in order to eliminate the catalyst. The filtrate was concentrated to dryness and 0.81 gm of methyl dl cis chrysanthemate were obtained.

(a) Reduction by diimide

Diimide was prepared, in situ, according to Van Tamelen et al, J.A.C.S. 83, 3725 (1961) starting from potassium azodicarboxylate.

1.15 gm of 3,3-dimethyl-2-(2′-methyl-1′-propenyl)-1-(methoxycarbonyl)-cyclopropene was introduced into a suspension of 1.4 gm of potassium azodicarboxylate in 80 cc of methanol, under an atmosphere of nitrogen. 800 μl of acetic acid were slowly added thereto, dissolution of the potassium salt was completed by adding another 100 microliters of acetic acid. The methanolic solution was concentrated to dryness and water was added to the residue. The aqueous phase was extracted with pentane. The organic phases were combined, washed with water, dried, and evaporated to dryness. 1.034 gm of the raw dl cis ester was obtained.

The raw dl cis ester was subjected to chromatography on silica gel with elution with a 99:1 mixture of petroleum ether (b.p. 40°–60° C.) and ethyl ether. 0.838 gm of methyl dl cis chrysanthemate were obtained.

EXAMPLE 2

Methyl ester of 2,2-dimethyl-3RS-(2'-methyl-1'-propenyl)-cyclopropane-1SR-carboxylic acid or Methyl ester of dl cis chrysanthemic acid STEP (A) Methyl ester of 5-methyl-hexa-2,4-dienoic acid 500 mg of the methyl ester of 5-methyl-hex-4-en-2-ynoic acid (prepared in Example 1) was hydrogenated in a hydrogenation bomb in the presence of 150 mg of Lindlar catalyst in suspension in 100 cc of ethyl acetate. After 15 minutes of hydrogenation, the expected product was obtained. The raw mixture containing the methyl ester of 5-methyl-hexa-2,4-dienoic acid was utilized as such for the next step of the synthesis.

STEP (B) Methyl ester of 4,5-dihydro-3,3-dimethyl-5-(2'-methyl-1'-propenyl)-3H-pyrazole-4-carboxylic acid and the Methyl ester of 4,5-dihydro-5,5-dimethyl-4-(2'-methyl-1'-propenyl)-1H-pyrazole-3-carboxylic acid The addition of diazo-2-propane onto the precedingly obtained raw ester of Step (A) was effected very slowly at 0° C. Diazo-2-propane was added until an excess was present in the reaction medium after completion of the reaction. The raw product obtained after evaporation of the solvent was recrystallized from ether/hexane mixture at −78° C. 420 mg of the methyl ester of 4,5-dihydro-5,5-dimethyl-4-(2'-methyl-1'-propenyl)-1H-pyrazole-3-carboxylc acid was isolated in the form of liquid at room temperature. The mother liquors were subjected to chromatography on silica gel with elution by a 25:75 mixture of ethyl ether and hexane. 240 mg of the methyl ester of 4,5-dihydro-3,3-dimethyl-5-(2'-methyl-1'-propenyl)-3H-pyrazole-4-carboxylic acid was isolated in the form of a pale yellow liquid after evaporation of the solvents.

STEP (C) The methyl ester of 2,2-dimethyl-3RS-(2'-methyl-1'-propenyl)-cyclopropane-1SR-carboxylic acid or the methyl ester of dl chrysanthemic acid After irradiation of the 120 mg of the methyl ester of 4,5-dihydro-3,3-dimethyl-5-(2'-methyl-1'-propenyl)-3H-pyrazole-4-carboxylic acid (from Step B above) in anhydrous ether under the condition described in Example 1, Step (D), 100 mg of a raw product were obtained.

This raw product was subjected to chromatography on silica gel with elution by a 5:95 mixture of ethyl ether and hexane. 95 mg of methyl dl cis chrysanthemate were recovered, identical to that obtained in Example 1.

By heating the methyl ester of 4,5-dihydro-3,3-dimethyl-5-(2'-methyl-1'-propenyl)-3H-pyrazole-4-carboxylic acid to 110° C. in toluene, the expected product, methyl dl cis chrysanthemate, was also obtained, containing however, about 30% of the dl trans derivative.

The preceding specific embodiments are illustrative of the practice of the invention. It is to be understood however, that other expedients known to those skilled in the art or disclosed herein may be employed without departing from the spirit of the invention or the scope of the appended claims.

We claim:

1. A process for the preparation of alkyl esters of 2,2-dimethyl-3RS-(2'-methyl-1'-propenyl)-cyclopropane-1SR-carboxylic acid, or alkyl esters of dl cis chrysanthemic acid having the formula

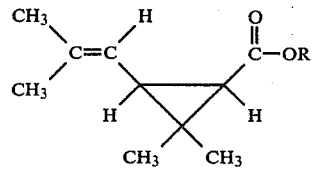

wherein R is an alkyl having from 1 to 6 carbon atoms consisting essentially of the steps of (A) reacting methyl lithium with 2-methyl-pent-2-en-4-yne in an inert organic solvent, (B) reacting the lithiated derivative obtained with a $C_1$-$C_6$ alkyl chloroformate at a temperature below 0° C. in an inert organic solvent, (C) recovering an alkyl ester of an unsaturated acid having the formula

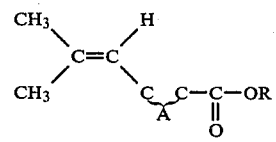

wherein R has the above assigned values and $\widetilde{A}$ represents a carbon to carbon bond selected from the group consisting of an ethylenic bond and an acetylenic bond, (D) reacting said alkyl ester of an unsaturated acid with diazo-2-propane at a temperature below 0° C. in an inert organic solvent, to obtain when $\widetilde{A}$ is an acetylenic bond a mixture of compounds having the formula selected from the group consisting of

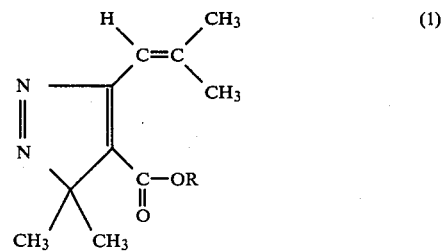

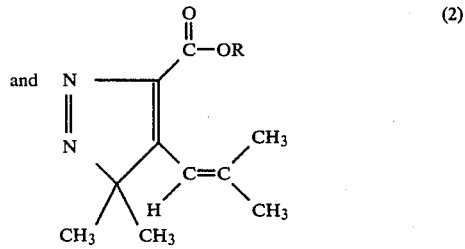

which can be separated, and when $\widetilde{A}$ is an ethylenic bond, a mixture of compounds having the formula selected from the group consisting of (3) 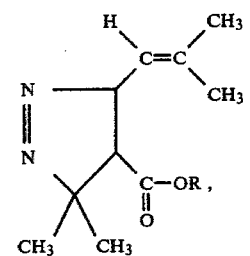

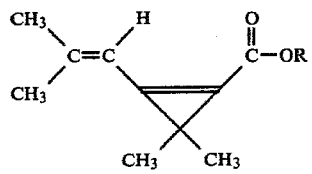

and (4) 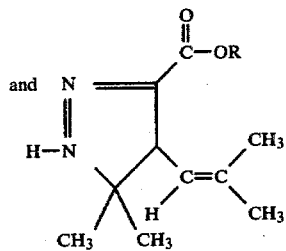

which are separated, (E) subjecting the alkyl ester of formula 1,2, or mixtures thereof to irradiation and of formula 3 to irradiation and heating, and (F) recovering said alkyl esters of dl cis chrysanthemic acid.

2. The process of claim 1, steps E and F wherein said alkyl ester of a pyrazole carboxylic acid is formula 1,2, or mixtures thereof and the product resulting from the said irradiation step is a cyclopropene having the formula wherein R has the above assigned values, which is reduced by the action of a reducing agent selected from the group consisting of (a) hydrogen in the presence of nickel-boride, (b) hydrogen in the presence of palladium deposited on calcium carbonate and (c) diimide.

3. The process of claim 2 wherein said reducing agent is hydrogen in the presence of nickel boride "P-1", prepared in situ.

4. The process of claim 2 wherein said reducing agent is diimide.

5. The process of claim 1 step (B) wherein R is methyl and said lithiated derivative in solution in ether is introduced into an ethereal solution of methyl chloroformate at a temperature of $-55°$ C.$\pm 20°$ C., and, in Step (C), A is an acetylenic bond.

6. The process of claim 1 step (C) wherein said alkyl ester of an unsaturated acid has the formula wherein A is an acetylenic bond and said acetylenic bond is reduced by the action of a reducing agent to A is an ethylenic bond.

7. The process of claim 6 wherein said reducing agent is hydrogen in the presence of a Lindlar catalyst in an inert solvent.

8. The process of claim 1, step D, wherein said diazo-2-propane in solution in ether is introduced into an ethereal solution of said alkyl ester of an unsaturated acid at a temperature of $-60°$ C.$\pm 20°$ C.

9. The process of claim 1 step E, wherein said irradiation step is conducted in an inert organic solvent at a temperature of $+15°$ C.$\pm 10°$ C. employing a mercury vapor lamp.

10. The process of claim 1 step E, wherein said alkyl ester of a pyrazole carboxylic acid is formula 3 and said heating step is conducted at about 110° C. in the presence of an organic solvent.

* * * * *

UNITED STATES PATENT AND TRADEMARK OFFICE
CERTIFICATE OF CORRECTION

PATENT NO. : 4,233,129
DATED : November 11, 1980
INVENTOR(S) : Michel Franck-Neumann et al.

It is certified that error appears in the above—identified patent and that said Letters Patent is hereby corrected as shown below:

Column 4, line 48, "halogen" should read -- hydrogen --.

Column 7, Delete structural formula I, second occurrence.

Column 9, line 44, delete "(2'-".

Column 11, lines 43 and 44, "dl chrysanthemic" should read -- dl cis chrysanthemic --.

Signed and Sealed this

Twenty-eighth Day of April 1981

[SEAL]

Attest:

RENE D. TEGTMEYER

Attesting Officer

Acting Commissioner of Patents and Trademarks